(12) United States Patent
Hu et al.

(10) Patent No.: US 9,667,696 B2
(45) Date of Patent: May 30, 2017

(54) LOW LATENCY WEB-BASED DICOM VIEWER SYSTEM

(71) Applicant: More Health, Inc., San Mateo, CA (US)

(72) Inventors: Bo Hu, S. San Francisco, CA (US); Chaoyi Du, S. San Francisco, CA (US); Hope Lewis, San Mateo, CA (US); Xuannan Wang, San Mateo, CA (US); Robert Warren, San Francisco, CA (US); Robert Chang, Palo Alto, CA (US); Jeremy Gao, San Mateo, CA (US)

(73) Assignee: MORE HEALTH, INC., Foster City, CA (US)

( * ) Notice: Subject to any disclaimer, the term of this patent is extended or adjusted under 35 U.S.C. 154(b) by 244 days.

(21) Appl. No.: 14/657,511

(22) Filed: Mar. 13, 2015

(65) Prior Publication Data
US 2016/0267649 A1    Sep. 15, 2016

(51) Int. Cl.
| G06F 3/00 | (2006.01) |
| H04L 29/08 | (2006.01) |
| G06F 19/00 | (2011.01) |

(52) U.S. Cl.
CPC .............. *H04L 67/06* (2013.01); *G06F 19/32* (2013.01)

(58) Field of Classification Search
CPC .................................. H04L 67/06; G06F 19/32
See application file for complete search history.

(56) References Cited

U.S. PATENT DOCUMENTS

| | | | | |
|---|---|---|---|---|
| 2004/0249806 A1* | 12/2004 | Kanada | ................ | G06F 17/3028 |
| 2007/0165933 A1* | 7/2007 | Thomas | ................ | G06F 19/321 |
| | | | | 382/128 |
| 2008/0140722 A1* | 6/2008 | Jakobovits | ............ | G06F 19/321 |
| 2009/0185732 A1* | 7/2009 | Zhang | .................... | G06F 19/321 |
| | | | | 382/132 |
| 2013/0266242 A1* | 10/2013 | Dorn | ........................ | G06T 1/60 |
| | | | | 382/305 |
| 2014/0006926 A1* | 1/2014 | Yeluri | ................... | G06F 19/321 |
| | | | | 715/234 |
| 2014/0140637 A1* | 5/2014 | Rachev | ............. | G06F 17/30268 |
| | | | | 382/305 |

\* cited by examiner

*Primary Examiner* — Omar Abdul-Ali
(74) *Attorney, Agent, or Firm* — U.S. Fairsky LLP; Yue Xu (57) ABSTRACT

Systems and methods of the present invention enable low latency viewing of medical images over a network and therefore can fulfill the functionality that is required for an international DICOM viewing platform. The system includes a server and a client that communicates with each other in the background and reduces image viewing latency in multiple aspects. When a user contacts the server using a web browser, the server sends the client to the user's computer over the network. The client runs from the browser and will send signals to the server to allow the server to load data into memory from storage one or more steps before the user requests the data, reducing latency on the server. The client will download and cache image data one or more steps before the user begins to view the images, and as a result latency from network transmission is also reduced.

15 Claims, 13 Drawing Sheets

FIG.12

LOW LATENCY WEB-BASED DICOM VIEWER SYSTEM

CROSS REFERENCES TO RELATED APPLICATIONS

N/A

BACKGROUND OF THE INVENTION

Field of the Invention

The present invention relates to DICOM query/retrieve operations and a special storage method that accelerate the display of DICOM image over a network. More particularly, certain embodiments relate to a web-based DICOM viewer of an international experts co-diagnosis system that intelligently download large DICOM image meta data and pixel data, which are processed before the very first request on these certain objects, in stages by anticipating the possible image content request.

Description of the Related Art

Digital Imaging and Communications in Medicine (DICOM) is a standard for handling, storing, printing, and transmitting information in medical imaging. It includes a file format definition and a network communications protocol. The communication protocol is an application protocol that uses TCP/IP to communicate between systems. DICOM files can be exchanged between two entities that are capable of receiving image and patient data in DICOM format. The National Electrical Manufacturers Association (NEMA) holds the copyright to this standard. It was developed by the DICOM Standards Committee, whose members are also partly members of NEMA.

DICOM enables the integration of scanners, servers, workstations, printers, and network hardware from multiple manufacturers into a Picture Archiving and Communication System (PACS). The different devices come with DICOM conformance statements that clearly state which DICOM classes they support. DICOM has been widely adopted by hospitals and is making inroads in smaller applications like dentists' and doctors' offices.

The contents of the DICOM standard go far beyond a definition of an exchange format for medical image data. DICOM defines data structures for medical images and related data, network oriented services, e.g. image transmission, query of an image archive, print, and RIS-PACS-modality integration formats for storage media exchange, and requirements for conforming devices and programs.

The DICOM network services are based on the client/server concept. In case two DICOM applications are going to exchange information, they must establish a connection and agree on the following parameters: who is client and who is server, which DICOM services are to be used, and in which format data is transmitted (e.g. compressed or uncompressed). Only if both applications agree on a common set of parameters, the connection can and will be established. In addition to the most basic DICOM service "image transmission" there are a number of advanced services, e.g. the DICOM image archive service allows to search images in a PACS archive by certain criteria (e.g. patient, time of creation of the images, modality etc.) and to selectively download images from this archive, the DICOM print service allows to access laser cameras or printers over a network, so that multiple modalities and workstations can share one printer, the DICOM modality work list service allows to automatically download up-to-date work lists including a patient's demographic data from an information system to the modality.

However, the detailed implements of PACS are different from country to country. So far there is no national PACS network yet, much less an international one. Usually medical institutions purchase service and equipment from various venders and make the PACS physically isolated. The disadvantage of this architecture is that, although PACS's could exchange data between each other via DICOM protocol, users still suffer from the latency time in data transmission.

SUMMARY OF THE INVENTION

The present invention aims at providing a low latency web-based DICOM viewer of an International Experts Co-diagnosis System (IECS). With the architecture described in the present invention, doctors all around the world can access a centralized IECS to view DICOM images with low latency.

According to an embodiment of the present invention, there is provided a method for processing and storing case DICOM files, separating meta data and pixel data into different databases. The method includes: extracting meta data from case DICOM files and storing the structured data into a SQL database, extracting pixel data from case DICOM files, transforming the pixel data to base64 string, applying compression algorithm to the pixel string and storing the compressed pixel data string to a NOSQL database.

According to another embodiment of the present invention, there is provided a method of dynamically building DICOM meta blocks for client-side intelligent fast downloading. The method includes: building a DICOM file block for each DICOM file, which would be used for client-side intelligent fast downloading; dynamically loading DICOM meta data block for data that is regarded as active data to server memory according to a client-side signal and a specified rules set; and dynamically loading DICOM pixel data blocks for data that is regarded as active data to server memory according to the client-side signal and a specified rules set.

According to yet another embodiment of the present invention, there is provided a strategy that intelligently anticipates the possible coming request for specified DICOM files by collecting the client-side signal and fetching DICOM meta data and pixel data ahead of the actual requests. The method includes: sending a signal from client to server when a doctor accesses a patient case list; anticipating the viewing and downloading the meta data and pixel data of leading DICOMs files of the present case when the doctor accesses his/her case entry; anticipating the viewing and downloading the meta data and pixel data of other DICOM images of the present case when the doctor activates the built-in web based DICOM viewer.

In an embodiment of the invention, a computer-readable storage medium includes computer-readable server program code to be executed by a computer to implement a server, and client program code to implement a client. The computer-readable storage medium refers to one or more nonvolatile storage devices including but not limited to CD-Rom, magnetic hard disk drives, solid state drives, and USB drives. The computer can be any computer including server, work station, personal computer, or even tablet that can be configured as a server. The client program code is configured to be sent from the server to a user's computer via a network and run via a browser on the user's computer. The user's computer can be a work station, a personal computer, or a tablet. In an aspect of the embodiment, the client is programmed to send a signal to the server for the server to load pixel data for one or more medical images in a case into memory after the user begins to view the case and before the user commands to view the one or more medical images. Additionally, the client is programmed to download and cache pixel data for subsequent medical images in the background after the user begins to view the first medical image and before the user commands to view the subsequent medical images.

In an aspect of the embodiment, the client is programmed to retrieve the pixel data from the server to the user's computer for the first medical image after the user begins to view the case and before the user commands to view the first medical images. In another aspect, the medical images include pixel data and meta data, and the client is programmed to retrieve and cache pixel data for the first medical image, meta data for the first medical image, and thumbnails of more than one medical images for navigating through the more than one medical images, after the user begins to view the case and before the user commands to view the first medical images. In yet another aspect, the pixel data of the medical images is compressed before being sent to the client, and the client is programmed to decompress the medical image pixel data. In another aspect, the client program code includes asynchronous JavaScript and XML techniques and enables the client to communicate with the server asynchronously in the background. In various aspects, the client begins to download pixel data for the first medical image after the user begins to view a document list in the case. In other various aspects, the client is configured to preferentially download and cache pixel data for medical images adjacent in sequence to the medical image currently displayed. In another aspect, the client includes one or more components including a client viewer for displaying the medical images. When a user visits the IECS website, the program code for the various components of the client may be sent to the user's computer all at once or in stages. For example, the program code for the client viewer may be sent to the client's computer when the user begins to view a case, when the user begins to view medical images, or some time in between. In another aspect, the client viewer includes one or more functions including but not limited to zoom, pan, rotate, brightness adjustment, and ruler.

In another embodiment of the invention, a user may view medical images through a network by contacting a server using a local computer, receiving from the server a client that automatically runs on the local computer, and displaying a first medical image using pixel data retrieved by the client and cached on the local computer. The client is programmed to communicate with the server in the background asynchronously. After the user begins to view the content of a medical case, the client will send a user-in-case signal to the server. After receiving the user-in-case signal, the server will begin to load pixel data for the medical images in the medical case into memory. After the user begins to view a webpage in the case that includes a link for viewing medical images, the client will begin to retrieve pixel data for the first medical image from the server and cache the pixel data for the first medical image on the local computer.

In certain aspects of the embodiment, the network may be local area network or wide area network. In a further aspect, a user may contact the server using a web browser on the local computer. The client runs from the web browser, and the client does not require installation or uninstallation. In a yet further aspect, the pixel data of the medical images on the server is compressed, and the client decompresses the pixel data of the medical images once received on the local computer. In another aspect of the embodiment, asynchronous JavaScript and XML techniques are employed to enable the client to communicate with the server asynchronously in the background. In a further aspect, a client viewer is received from the server. The client viewer runs from the browser on the local computer, and the client viewer does not require installation or uninstallation. In a yet further aspect, the client viewer includes functions including zoom, pan, rotate, brightness adjustment, and ruler. In yet another aspect, the client is programmed to retrieve and cache pixel data of other medical images in the background when the first medical image is displayed by the client viewer.

BRIEF DESCRIPTION OF THE DRAWINGS

FIG. 4-1 and FIG. 4-2 are schematic diagrams that show preprocessing DICOM files.

DETAILED DESCRIPTION OF THE INVENTION

Persons of ordinary skill in the art will realize that the following description is illustrative only and not in any way limiting. Other modifications and improvements will readily suggest themselves to such skilled persons having the benefit of this disclosure.

In an embodiment of the invention, an International Experts Co-diagnosis System ("IECS") provides a collaborative platform for medical experts all around the world. Resources of IECS are managed as case-centralized style. The system includes a central server and a client. Case data is stored at the center server, and the client is sent to users via a network and runs in the users' browser. The network may be internet that runs across the World Wide Web or a local area network. Medical service providers such as doctors, and customers such as patients, access IECS through the network using a web browser. Common web browsers include Internet Explorer, Firefox, Opera, and Google Chrome and are software applications for retrieving, presenting, and sending information on the World Wide Web. The server not only sends passive or interactive webpages that are displayed on the user's browser but also sends the client that runs inside the web browser. The client may have functions like an installed software application but does not require installation or uninstallation. In some aspects of the embodiment, the client includes JavaScript and XML (AJAX) techniques and asynchronously communicates with the server in the background without interference with the browser to display webpages.

Figure 1:
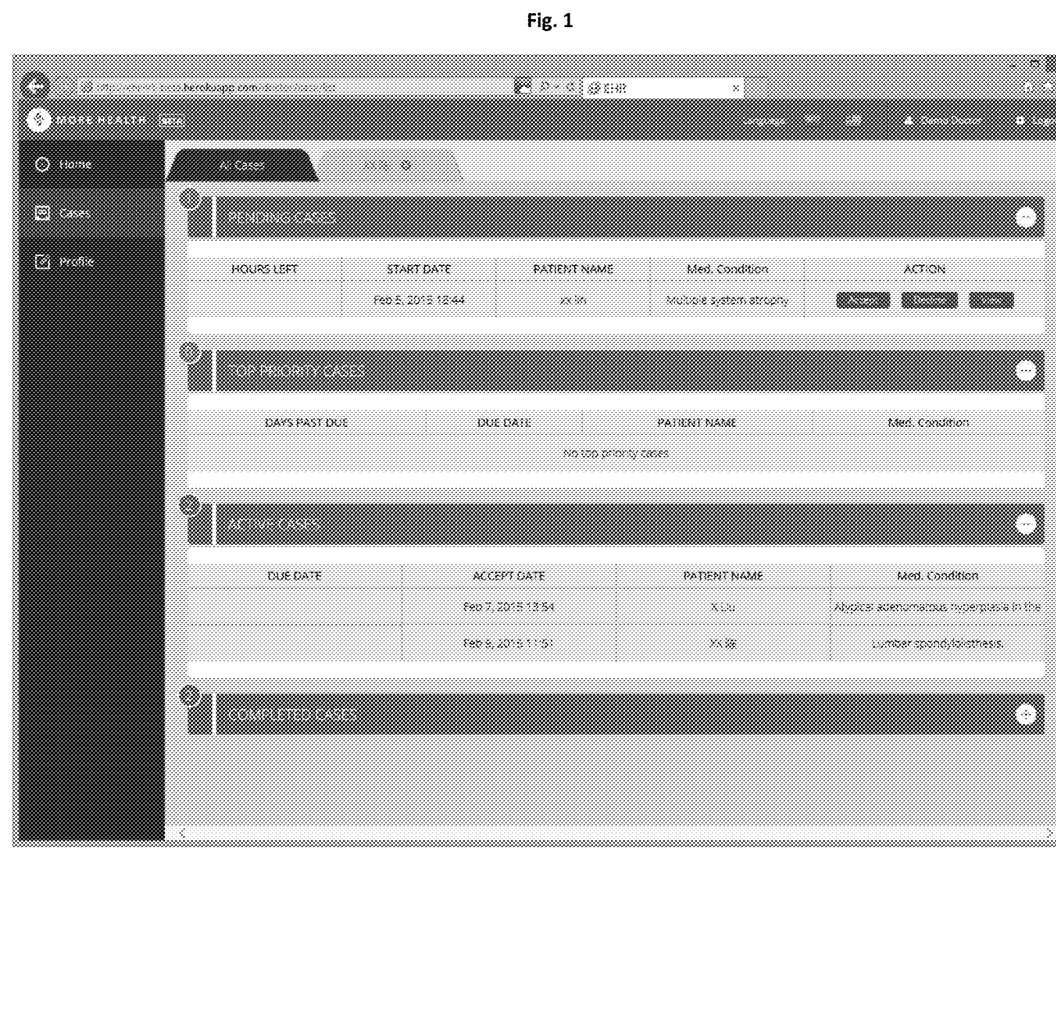
FIG. 1 is a screenshot of a case list in an International Experts Co-diagnosis System.
Figure 2:
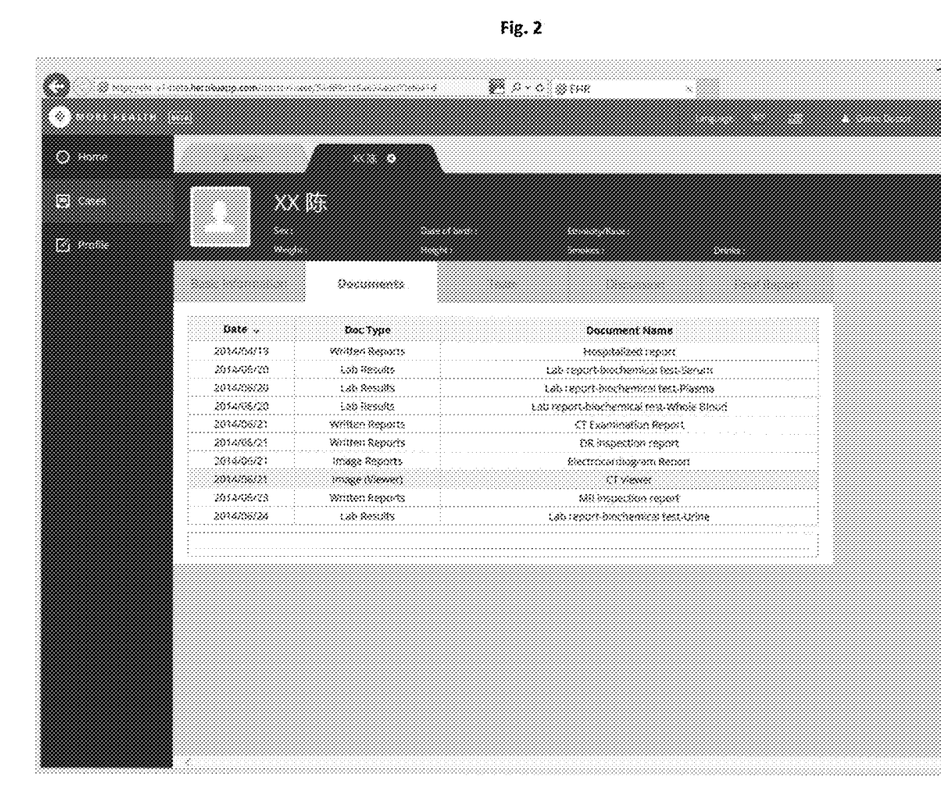
FIG. 2 is a screenshot of a document list in an International Experts Co-diagnosis System.

In an aspect of the embodiment, an authorized doctor will need to sign up for a doctor's account on the IECS. When the authorized doctor signs into his/her account, a case list listing authorized cases assigned to the doctor can be displayed. For example, the case list in FIG. 1 lists pending cases, top priority cases, active cases, and completed cases, if there is any. Each case usually includes one patient although it may include a group of related patients. The case list may display brief information of each authorized case entry including status, patient name, medical condition, and start date. Clicking on an authorized case entry will lead to the case's detailed information page. In another aspect of the embodiment as shown in FIG. 2, a document list of the present case including written reports from various dates, lab results from various tests and dates, image reports, and medical images may be displayed and function as a gateway for displaying the listed documents. Each entry in the document list may include a link to the document itself. The doctor may view the document by clicking on the document entry in the list. The entry "Image" may include a link to an image viewer for viewing medical images.

Figure 3:
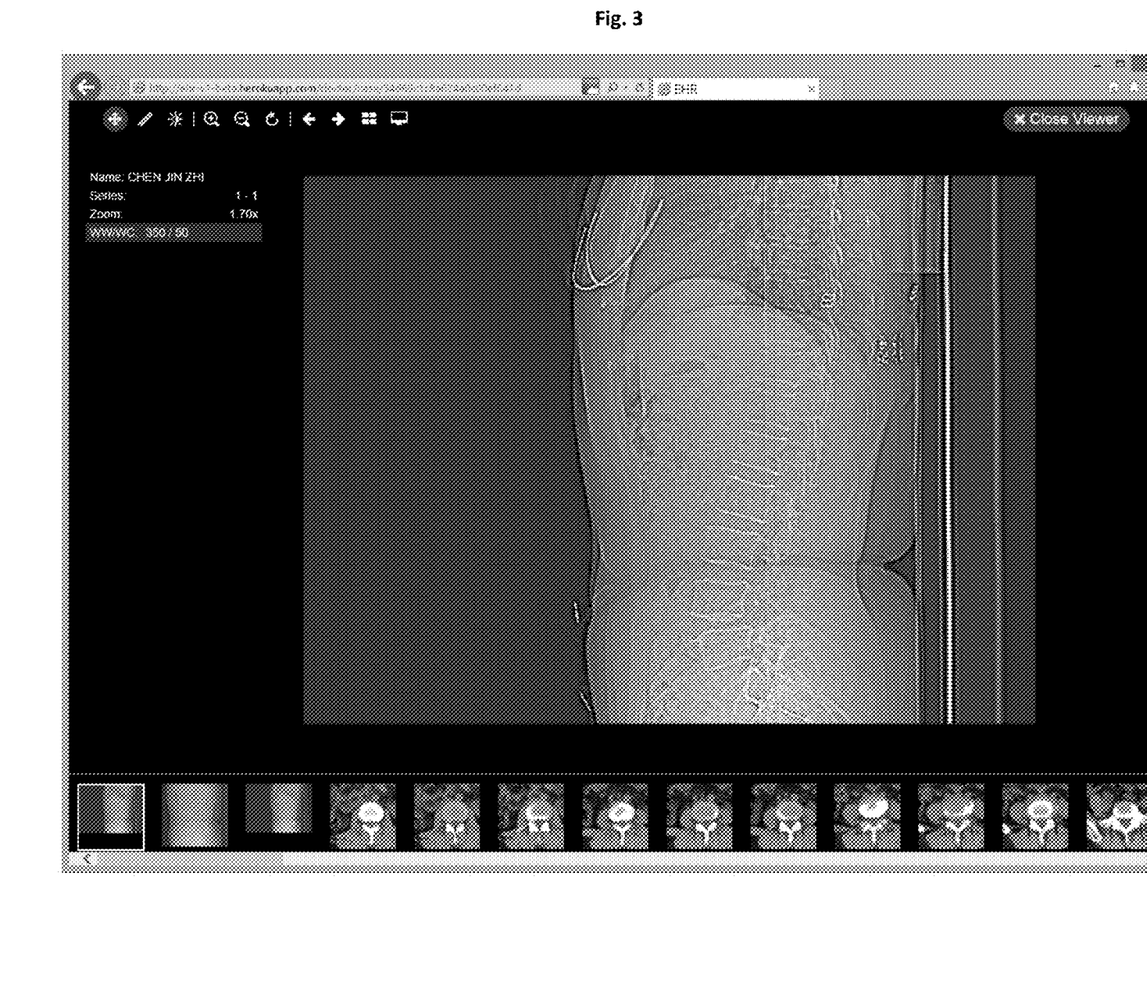
FIG. 3 is a screenshot of a client viewer in an International Experts Co-diagnosis System that implements the current invention.

FIG. 3 shows a screen of an image viewer that is launched after clicking on the medical images entry. The image viewer window may reside within a web browser window, or it can be a new pop up window that does not show any web browser feature. In an aspect of the embodiment as shown in FIG. 3, the image viewer screen includes function buttons for image viewing functions including pan, ruler, brightness, zoom, rotate, and image navigation functions including previous, next, grid view, and full screen. In another aspect, the image viewer may display meta data together with the image itself. In another aspect, the viewer screen may include a navigation bar that includes thumbnails of medical images. Clicking a thumbnail will cause the corresponding full resolution image to be displayed. If there are more thumbnail images than that can be displayed in one screen, a scroll bar may be included for scrolling through the thumbnails.

Medical images are typically in DICOM format and are several megabytes in size, and each patient may have tens or even hundreds of DICOM images. In a case of 100 images at 5 MB each, the images will total 500 MB. The typical read speed from hard disk is about 100 MB/s, so it will take several seconds for the server of IECS to read the data from storage. Internet speed varies from a few hundred Kbps up to 15 Mbps for DSL and 100 Mbps for cable, and the speeds across regions especially in foreign countries vary widely. For reference, the average American home gets about 10 Mbps. To calculate the time required for downloading, the "bit" in the measures of mega bit per second needs to be divided by 8 to get in line with the "byte" in file sizes. Therefore, even at 100 Mbps, to download 500 MB of files, it takes 8*500/100=40 seconds. If the speed is only 10 Mbps, it will take 400 seconds or near 7 minutes to download the images. Obviously, low latency DICOM viewer functionality is critical to an international platform like IECS. Otherwise the doctors in a different country or area will suffer from communication obstacle.

The methods and systems of the current invention will shorten downloading time of IECS at multiple stages. Patient data including DICOM data are pre-processed. Through pixel data compression, intelligent anticipatory data downloading, and data caching, DICOM image downloading and rendering are accelerated. Additionally, IECS is multi-platform compatible because DICOM image rendering at client side adopts the HTML5 Canvas element.

Figure 41:
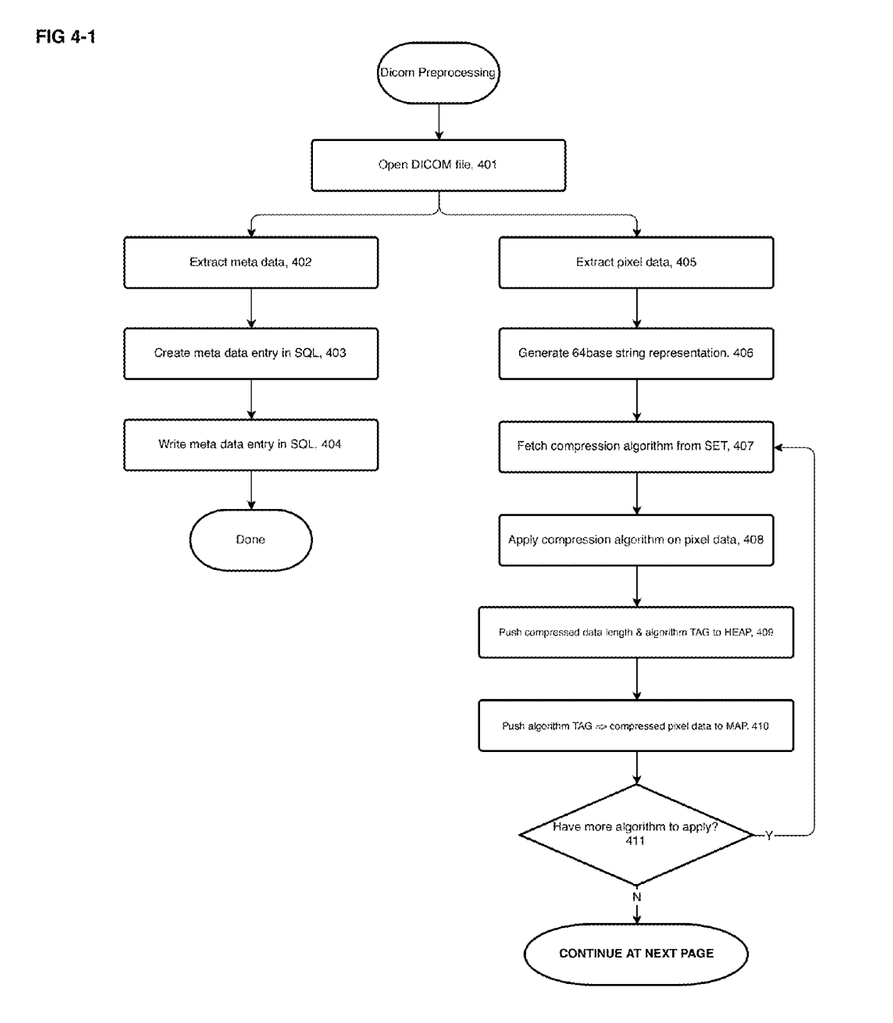

Patient data is centrally stored. New cases are recorded in the server's storage, and raw DICOM files of new cases are pre-processed before being served to remote users via a network. In an embodiment illustrated in FIG. 4, a server pre-processing module opens the raw DICOM files related to the new case, 401. The meta data from the DICOM files are extracted, 402. Because the IECS will collect DICOM data created from hardware manufactured from different countries, the data format of the extracted meta data will vary. For example, meta data extracted from Chinese DICOM files may contain GB2312 or GB18030 encoding. The difference in data encoding will cause codes incompatible to the client computer to display improperly. To achieve cross-platform compatibility, all meta data are transformed to Unicode encoding employing the most commonly used utf-8 encoding. A meta data entry is then created in a SQL database, 403, and the meta data is written into the meta data entry, 404. A relationship between the new meta data entry and related case database entries is also created.

The pixel data of DICOM files are extracted, 405. A thumbnail image is created for each of the DICOM images, and the pixel data is transformed to base64 string and stored in the server memory, 406. The pixel data of a DICOM image is typically several thousand KB. Because of the large file size, there may be a large transmission delay if the client side requests a large number of DICOM images. International transmission of data via the internet can be especially slow at times due to variability in connection speed. In comparison, compression and decompression speed is fast because of the advances in CPU and memory in personal computers. Therefore, the pixel data is compressed before transmitting to a client to reduce transmission delay. Several compression algorithms are applied to pixel data string and the most compressed data is stored to NOSQL database with a token that represents the applied compression algorithm.

Figure 42:
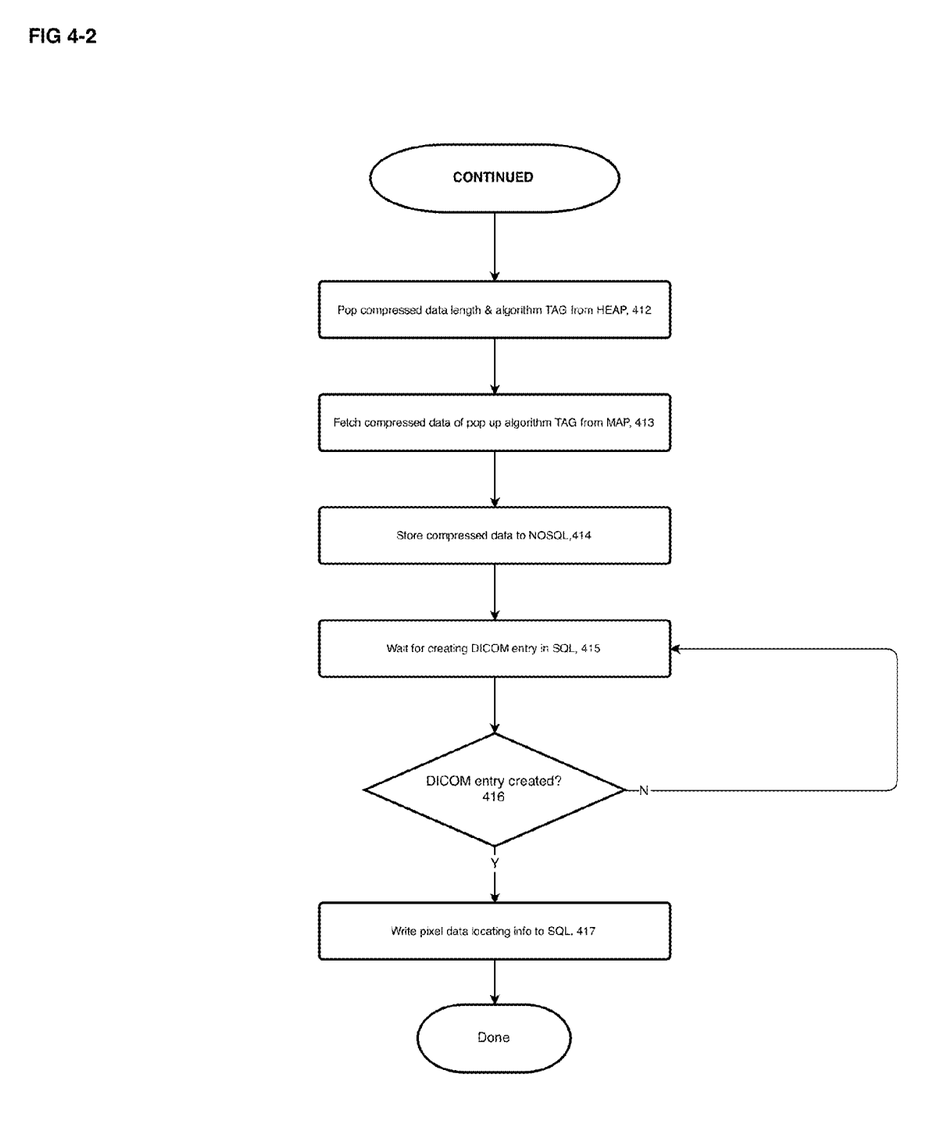

Again referring to FIG. 1, a compression algorithm is fetched from SET, 407. The compression algorithm is applied to the pixel data, 408, and the compressed data length and algorithm tag are pushed to HEAP, 409. The algorithm tag corresponding to compressed pixel data is further pushed to MAP. The pre-processing module then determines whether there is more compression algorithm to apply, 411. If there is, then an additional compression algorithm is fetched from SET, 407, and the process is repeated one more time. When all the compression algorithms have been applied, there are several versions of the compressed pixel data each resulted from a different compression algorithm. In an aspect of the embodiment, the compression algorithms include lossless compression algorithms including LZMA, LZO, DEFLATE, and bzip2. The compressed data lengths and algorithm tags are popped from HEAP, 412, and compared to each other in size. The smallest compressed data and its corresponding algorithm tag are fetched from MAP, 413, and stored in a NOSQL database, 414. The DICOM entry in the SQL database including the meta data corresponding to the compressed pixel data is looked up. If it is not found, the system will wait for a preset amount of time and look for it again, 415. When the DICOM entry is found to be created, 416, the thumbnail image, the applied compression algorithm tag, and the locating information for the compressed pixel data are written into the corresponding DICOM meta data entry in the SQL, 417.

In some aspects of the embodiment, at least two types of databases are employed, a SQL database and a NOSQL database. The NOSQL database is used for storing the pixel data, and the SQL database is used for storing the DICOM meta data, thumbnail image, compression algorithm tag, and the locating information for the pixel data. The advantage of the SQL database is that data can be easily organized and quickly searched, but a SQL database is slow when an entry is big such as the pixel data of a DICOM image. In comparison, a NOSQL database is faster in handling large files but not so adapt at organizing large databases with many entries. By utilizing a NOSQL database and a SQL database together, both fast retrieval of pixel data and organization of meta data are achieved.

The nature of lossless compression algorithm is to shorten data length without loss of information using the repeating pattern in the sequence information. Different compression algorithms have different advantages and disadvantages. We found that different compression ratios were obtained by using different compression algorithms including LZMA, LZO, DEFLATE, and bzip2, and it is unpredictable which algorithm will give the highest compression ratio. Therefore, several compression algorithms are tested for each DICOM image, and the one with the highest compression ratio is used. To facilitate decompression at the client side, a tag is created indicating the method of compression. By compressing and storing the image data before the image data is requested and delivered, valuable time is saved during data transmission over the internet.

Figure 5:
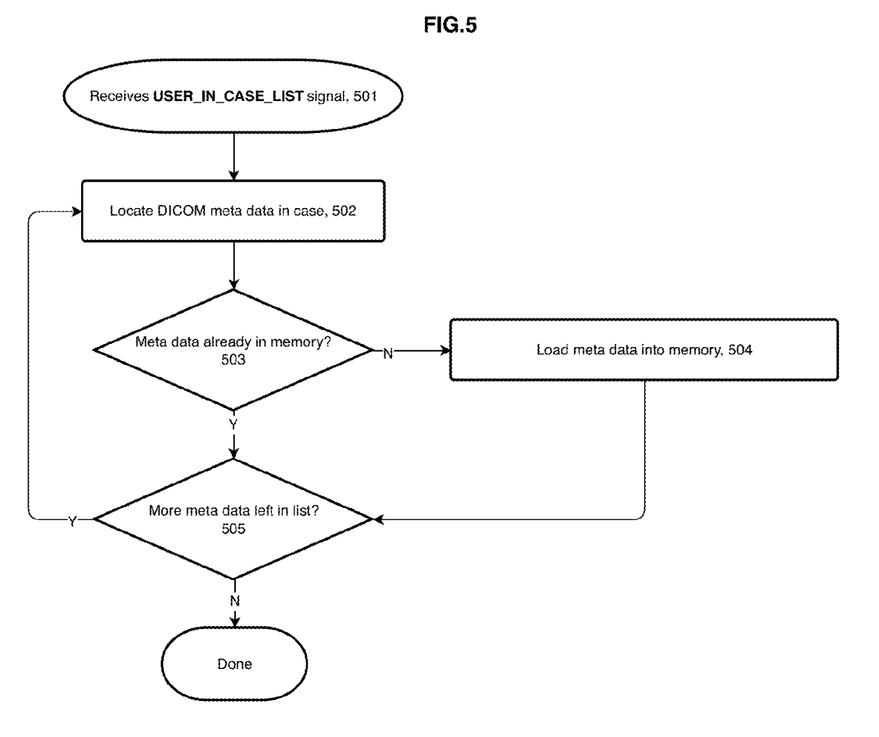
FIG. 5 is a schematic diagram showing a server logic flow relating to the response to a User-In-Case-List signal.

Image viewing latency is further reduced through intelligent anticipatory downloading. By selectively downloading image files ahead of time in the background, user experience is improved. The process begins as soon as a doctor logs into his/her account in IECS. In an embodiment as shown in FIG. 5, when a doctor accesses his/her case list in IECS, the client side will send a User_in_Case_List signal to the server side to inform that the user is viewing his/her case list, 501, and it is possible that all of the doctor's cases will be retrieved in the near future. As a result, the server side will begin to load DICOM meta data files for all of the cases listed for the current doctor into memory from hard disk, to speed up the possible coming retrieving. The server will begin by locating meta data for each of the cases in the current doctor's case list, 502. If the meta data of a case is not in the memory, 503, the required meta data will be retrieved from hard disk storage and loaded into memory, 504. The system will then check if there are more cases, 505, and if so it will go back to locate the meta data for the next case. The process repeats until the meta data for all the cases in the doctor's case list are loaded into memory from hard disk. Usually this part will be done when the doctor is still viewing the case list view, for example FIG. 1. When the doctor decides to access the detail page of a case by clicking on a case entry, all of the DICOM meta data files related to the case are already loaded into memory and ready for downloading, accelerating access by the client side.

Figure 6:
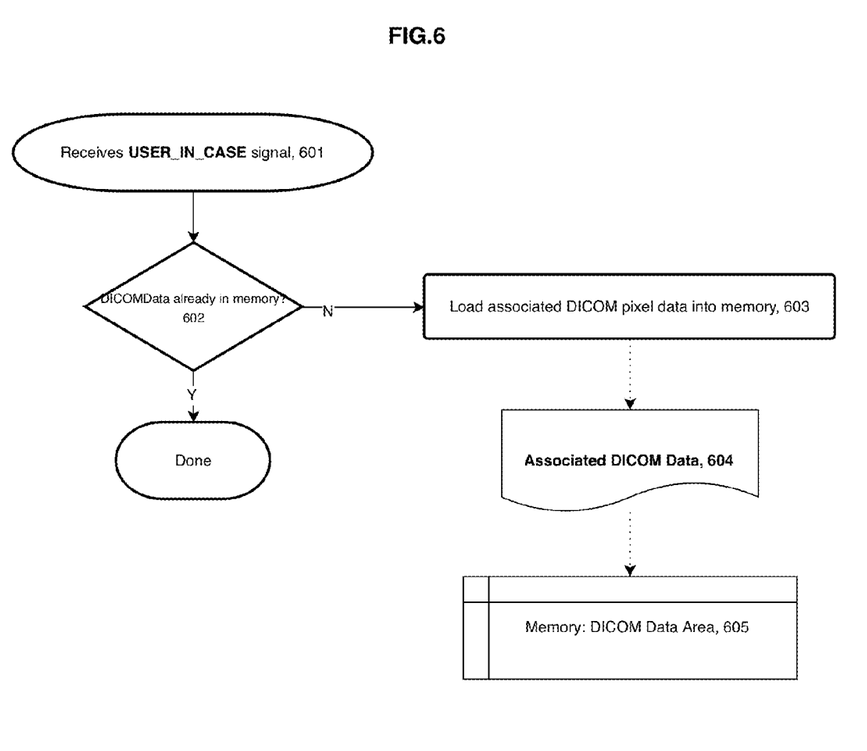
FIG. 6 is a schematic diagram showing a server logic flow in response to a User-In-Case signal.

A detailed information page for a current case may be displayed after a user clicks on the corresponding case entry in the case list. Information for the current case may be organized under several tabs including basic information of the patient, documents, medical team related to the case, discussion, and the doctor's own reports, for example FIG. 2. In an embodiment for faster processing as shown in the schematic diagram FIG. 6, as soon as the case's detailed information page is displayed, the client sends to the server a User_in_Case signal, 601. The signal includes information about the user and the case. The server then begins to load information related to the case into memory. The DICOM image data is likely to be large and time consuming to load from hard disk, so the server will check whether DICOM image data is already read into memory, 602. If the image data is not already in memory, the server will read it from storage into memory, 603, along with associated DICOM data 604, and temporarily store in memory in a designated DICOM data area 605. Because serving the data to a client from memory is faster than serving from hard disk storage, valuable time will be saved if the client requests DICOM image data as anticipated.

Figure 7:
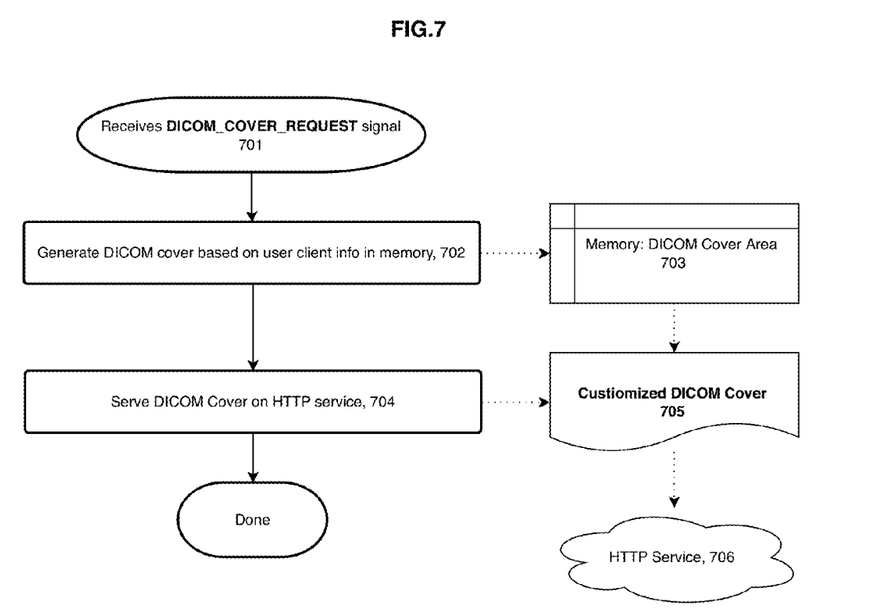
FIG. 7 is a schematic diagram showing a server logic flow in response to a DICOM-Cover-Request signal.

When a user of the IECS system is reading the case detail pages of a case, the system of the current invention may anticipate that the user will next access the DICOM documents of the case. As shown in FIG. 7, the client side will send a DICOM_Cover_Request signal, and the server will receive the signal for generating a DICOM cover page 701. DICOM cover page is the first page that is displayed after the user clicks the "DICOM Viewer" link. In other words, the cover page is the first display page for the DICOM image viewer. In some embodiments, the DICOM cover page includes the meta data for a first DICOM image, the first DICOM image, and thumbnail images of other DICOM images displayed as a navigation bar for the images in the current case, for example FIG. 3. The thumbnail images are displayed in a predetermined sequence such as image ID, name, size, and date. The system then generates the DICOM cover based on user information in memory 702, and saves it in the memory in DICOM cover area 703. When the client requests the DICOM cover, the server sends the DICOM cover to the client on HTTP service 704. The user may change the parameters of the DICOM cover and generate customized DICOM cover 705, which will be served to client via HTTP service 706.

The client DICOM viewer (the "client viewer") is written in Javascript and conforms to the Document Object Model (DOM). When a user clicks the image viewer link in the user's account, the client viewer is sent from the server of the IECS to the user's computer via internet and runs inside the user's internet browser. Because the client viewer adopts the HTML5 Canvas element, the client viewer is compatible on multiple platforms. Even though personal computer running the Windows system is described in the embodiments described below, the client viewer can be optimized for smart phones or tablets with very minor modifications. Asynchronous JavaScript and XML (AJAX) techniques are employed and enable the client viewer to send data to and retrieve data from the server asynchronously in the background without interfering with the display and behavior of the viewer.

Figure 8:
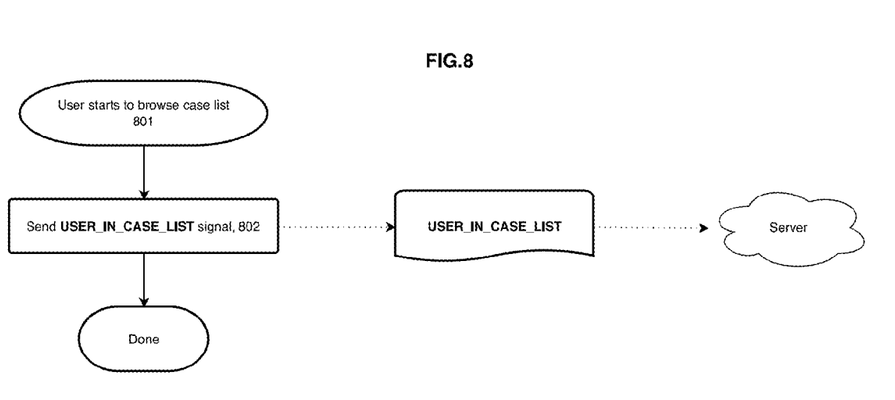
FIG. 8 is a schematic diagram showing a client logic flow in sending a User-In-Case-List signal.

An intelligent downloading mechanism is enabled on the client side of the IECS. Thus, the client will send information to the server and retrieve files from the server in the background in an asynchronous way, reducing apparent latency to the user. In an embodiment as shown in FIG. 8, when the user logs into his/her account at the IECS website, the server sends the client to the user's web browser. When the user starts to browse the case list in his/her account, 801, the client sends a User_in_Case signal to the server, 802. The signal includes information about the user and case list.

Figure 9:
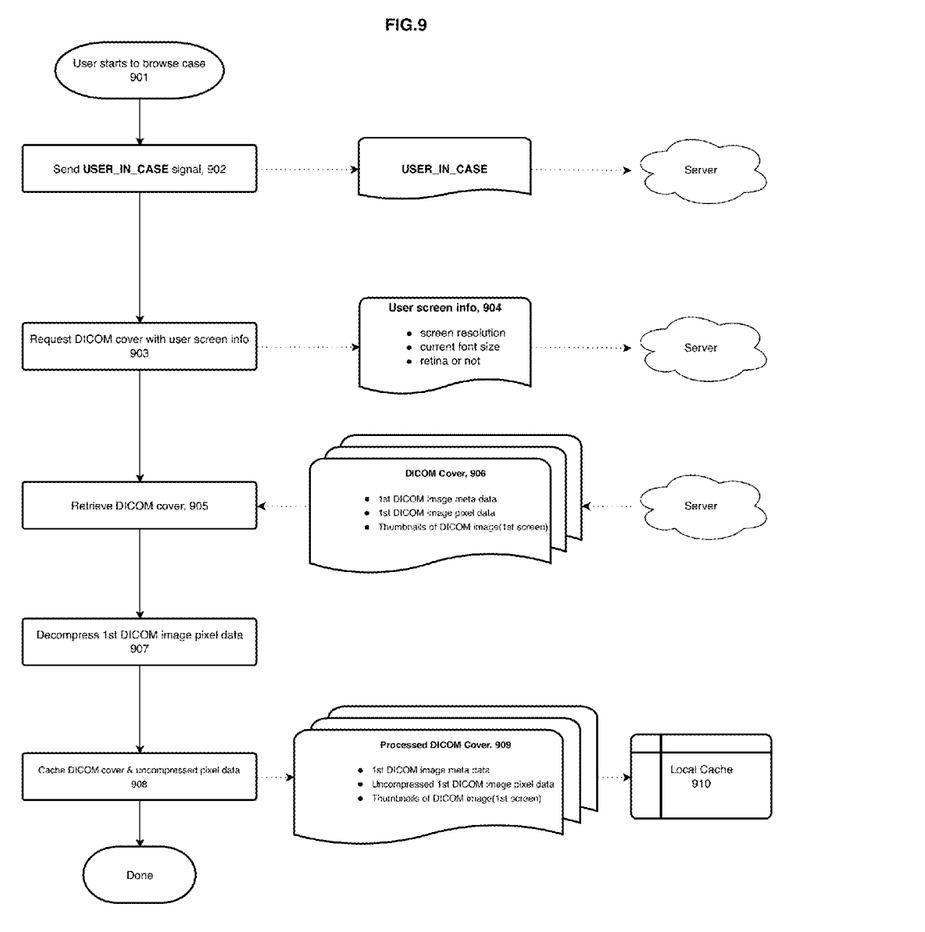
FIG. 9 is a schematic diagram showing a client logic flow for retrieval and cache of DICOM cover.

In another embodiment as shown in FIG. 9, when a user starts to browse a case 901, the client sends a User_in_Case signal to the server, 902. The signal includes information including the user and the case. Upon receiving the signal, the server is program to send a web page that include basic information on the current case including document list, team, discussion, and reports. The user will generally spend a minute or several minutes to read through. At the same time, the client sends a request for DICOM cover to the server 903. The request includes user screen information including screen size and resolution, current font size, and whether the screen has retina function 904. The server then prepares the DICOM cover files custom tailored to the user screen information including the first DICOM image pixel data, the first DICOM image meta data, and a number of thumbnail images that fit the DICOM cover page 906, and the client retrieves the files to the client computer's memory 905. The DICOM image pixel data is compressed by one of the lossless compression methods, and the meta data has information on the compression method. The client decompresses the DICOM image pixel data according to the compression method 907. The client then caches the data for the DICOM cover page 908 including the uncompressed pixel data for the first image, meta data for the first DICOM image, and thumbnails of DICOM images 909 into local cache 910.

Figure 10:
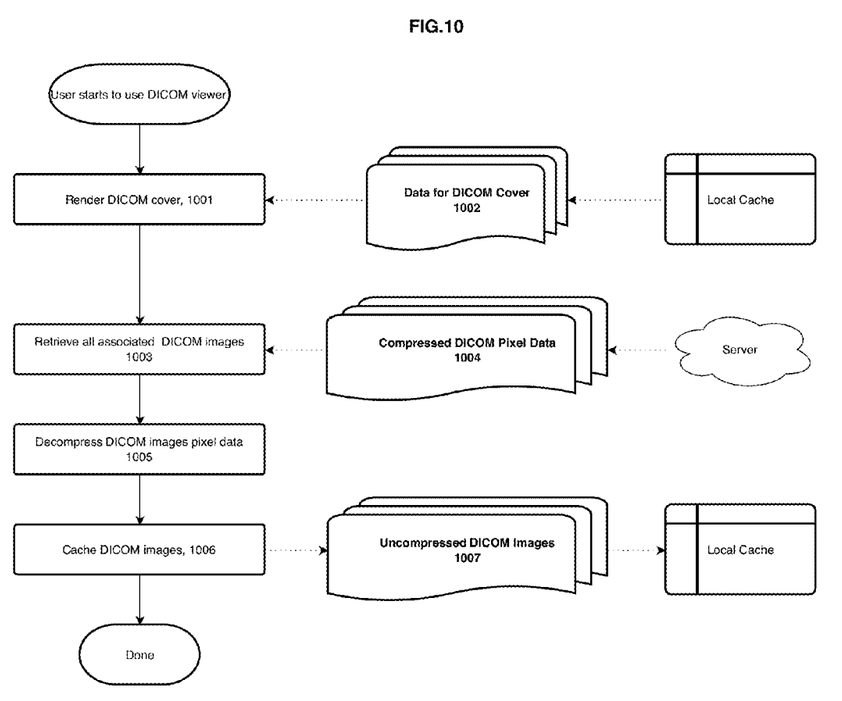
FIG. 10 is a schematic diagram showing a client logic flow for displaying DICOM images.

The intelligent downloading mechanism continues to work in the background, as shown in another embodiment illustrated in FIG. 10. When the doctor launches the DICOM viewer for the current case, the viewer renders the DICOM cover without delay from internet traffic 1001 because the viewer retrieves the data from local cache 1002. When the doctor is still examining the first DICOM image or meta data on the DICOM cover, the client continues to download pixel data and meta data of other DICOM images 1003. The pixel data files are already compressed and loaded in the server's memory 1004, so the downloading is accelerated on the server side. The client decompresses each pixel data file according to its corresponding compression method, which is indicated in the corresponding meta data 1005. The DICOM images including uncompressed pixel data and meta data 1007 are cached in local cache 1006, ready for displaying by the client viewer.

Figure 11:
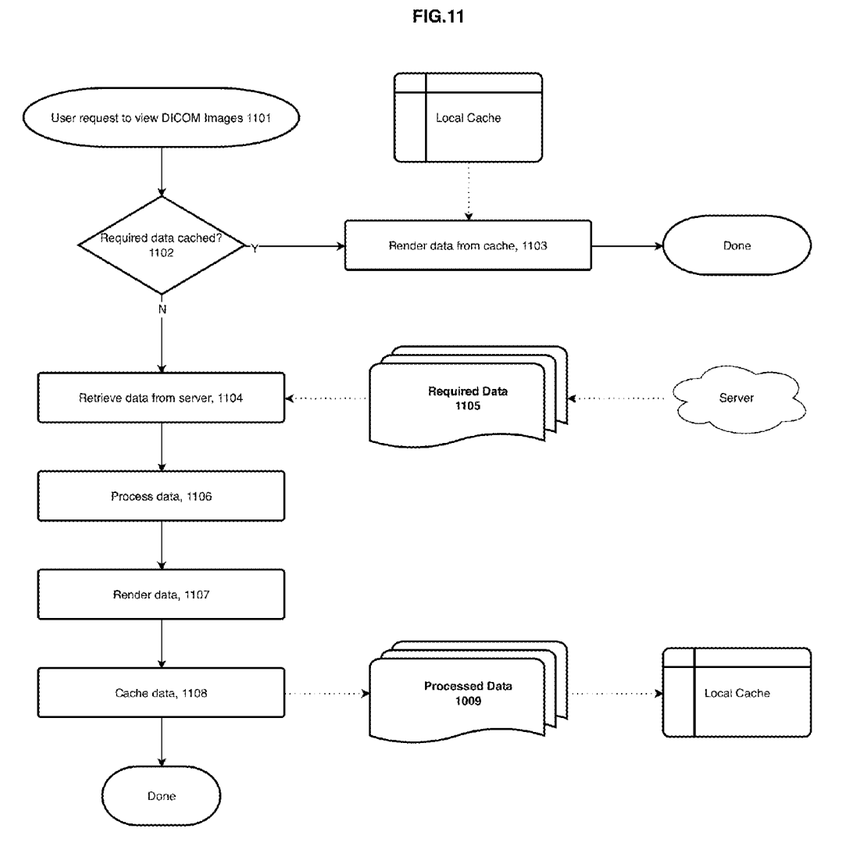
FIG. 11 is a schematic diagram showing a client logic flow for cache of data into local cache and use of data stored in local cache.

DICOM images are downloaded continuously, and the images that are close in sequence to the currently displayed image are downloaded and cached first. However, there may be a large number of images, and as a result it is possible that not all images are cached when the user requests to view it. There needs a method to locate the required image data, which is illustrated by an embodiment shown in FIG. 11. When a user requests to view a DICOM image by clicking on the image's thumbnail 1101, the client viewer first determines whether the required data is stored in cache 1102. If the image data is already cached, the viewer renders data from local cache 1103, and the user can view the image experiencing little latency. However, if the image pixel data is not already cached, the client viewer will have to retrieve the image pixel data from the server 1104. The required data should be already loaded in the memory of the server from the server's storage, and because the data is compressed, the data can be downloaded with minimal latency. The client viewer then decompresses the image pixel data 1106 and renders the DICOM image 1107. The decompressed image data is cached in the client computer for later viewing 1108. Thus, when the user views some other images and comes back, the same image data does not have to be downloaded from the server again.

Figure 12:
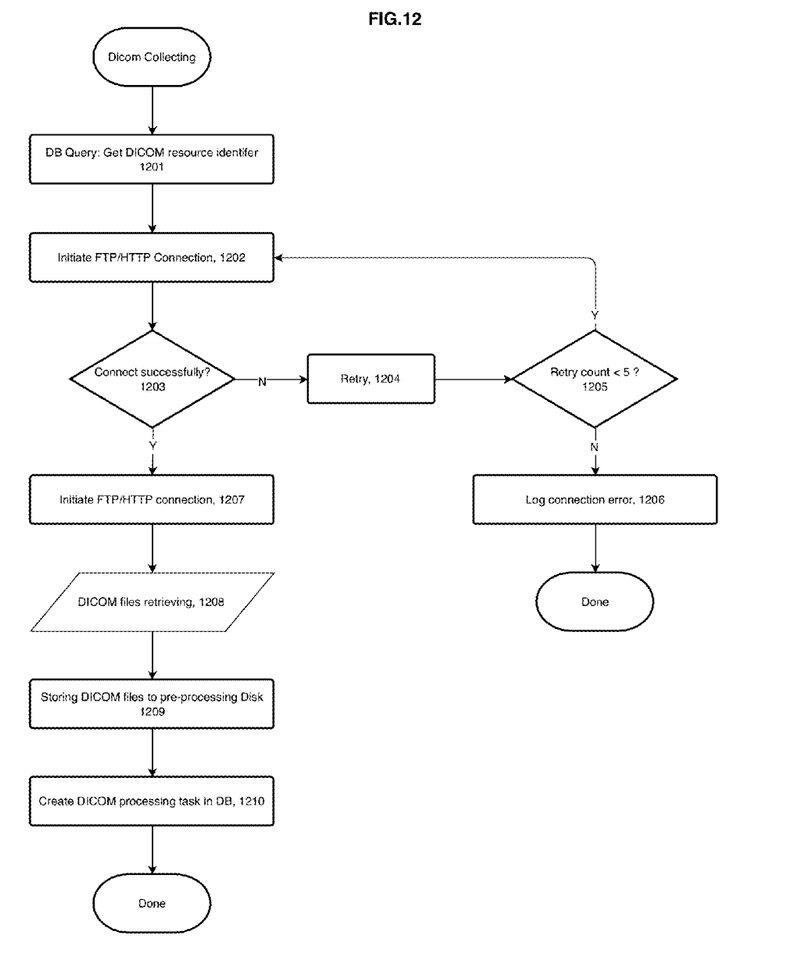
FIG. 12 is a schematic diagram showing a process for collecting DICOM data from a server to a user's computer.

An embodiment shown in FIG. 12 illustrates a method by which the client and the server communicate in the background to download the DICOM files. The process begins with the client obtaining the DICOM resource identifiers and creating a database query for downloading the DICOM files 1201. In some aspects of the embodiment, the image pixel data files for the images next in sequence to the currently displayed image, particularly the images whose thumbnails are currently displayed on the screen, are moved to the top of the query. The query will dynamically follow what the user displays on the screen. Downloading of files begins from the top of the query and uses either FTP or HTTP connection 1202. First the client determines whether the connection is successful for the file 1203. If it is not, the client will retry 1204, for a certain set of times, for example 5 times 1205. After the maximum number of retries, the client will log a connection error 1206, and skip the file. If the client connects successfully with the server for the particular file, a FTP or HTTP connection is initiated 1207, and the DICOM file retrieving begins 1208. When the downloading of the current file is completed, the client will begin to download the next file, and the above process repeats until all the DICOM files for the current case are downloaded. The downloaded file is stored to pre-processing disk 1209. A task for processing the newly downloaded file is created in a database 1210. For example, a compressed image pixel data file needs to be decompressed, and a task is recorded in the database accordingly.

This architecture is a promising way to implement a Low Latency Web-based DICOM Viewer System which could fulfill the functionality that provides an international DICOM viewing platform for doctors all around the world.

While embodiments and applications of this disclosure have been shown and described, it would be apparent to those skilled in the art that many more modifications and improvements than mentioned above are possible without departing from the inventive concepts herein. The disclosure, therefore, is not to be restricted except in the spirit of the appended claims.

What is claimed is:

1. A computer-readable storage medium including computer-readable server program code to be executed by a computer to implement a server, and client program code to implement a client, wherein:
   the client program code is configured to be sent to a user's computer via a network and run via a browser on the user's computer;
   the client is programmed to send a signal to the server for the server to load pixel data for one or more medical images in a case into memory after the user begins to view the case and before the user commands to view the one or more medical images;
   the client is programmed to download pixel data for subsequent medical images in the background after the user begins to view the first medical image, before the user commands to view said subsequent medical images;
   the medical images include pixel data and meta data; and
   the client is programmed to retrieve the pixel data for the first medical image, meta data for the first medical image, and thumbnails of more than one medical images for navigating through the more than one medical images, after the user begins to view the case and before the user commands to view the first medical images.

2. The computer-readable storage medium of claim 1, wherein:
   the pixel data of the medical images is compressed before being sent to the client, and
   the client is programmed to decompress the medical image pixel data.

3. The computer-readable storage medium of claim 1, wherein:
the client program code includes asynchronous JavaScript and XML techniques and enable the client to communicate with the server asynchronously in the background.

4. The computer-readable storage medium of claim 1, wherein:
the client is programmed to begin to download pixel data for the first medical image after the user begins to view a document list in the case.

5. The computer-readable storage medium of claim 1, wherein:
the client is configured to preferentially download pixel data for medical images adjacent in sequence to the medical image currently displayed.

6. The computer-readable storage medium of claim 1, wherein:
the client includes one or more components including a client viewer for displaying the medical images.

7. The computer-readable storage medium of claim 6, wherein:
the client viewer includes one or more functions selected from the group consisting of zoom, pan, rotate, brightness adjustment, and ruler.

8. A method for viewing medical images, comprising:
contacting a server through a network using a local computer;
receiving a client from said server, said client running on the local computer; and
displaying a first medical image using pixel data retrieved by said client and stored on the local computer, wherein:
said client is programmed to communicate with said server in the background asynchronously;
said client is programmed to send a user-in-case signal to the server after the user begins to view the content of a medical case;
said server is programmed to load pixel data for the medical images in the medical case into memory after receiving said user-in-case signal; and
said client is programmed to begin retrieving pixel data for the first medical image from the server and caching said pixel data for the first medical image on the local computer after the user begins to view a webpage in the case that includes a link for viewing medical images.

9. The method of claim 8, wherein:
the network is local area network or wide area network.

10. The method of claim 8, comprising:
contacting the server using a web browser on the local computer, wherein:
said client runs from said web browser, and
said client does not require installation or uninstallation.

11. The method of claim 8, wherein:
the pixel data of the medical images on the server is compressed, and
the client decompresses the pixel data of the medical images once received on the local computer.

12. The method of claim 8, wherein:
asynchronous JavaScript and XML techniques are employed to enable the client to communicate with the server asynchronously in the background.

13. The method of claim 8, further comprising:
receiving a client viewer from the server, wherein
the client viewer runs from the browser on the local computer, and
the client viewer does not require installation or uninstallation.

14. The method of claim 13, wherein:
the client viewer includes one or more functions selected from the group consists of zoom, pan, rotate, brightness adjustment, and ruler.

15. The method of claim 14, wherein:
the client is configured to retrieve pixel data of other medical images in the background when the first medical image is displayed by the client viewer.

* * * * *